United States Patent
Cardinault

(10) Patent No.: US 10,532,075 B2
(45) Date of Patent: *Jan. 14, 2020

(54) USE OF A PARTICULAR EXTRACT OF PROPOLIS FOR COMBATING THE SIDE EFFECTS OF CHEMOTHERAPY

(71) Applicant: POLLENERGIE, Saint-Hilaire-de-Lusignan (FR)

(72) Inventor: Nicolas Cardinault, Agen (FR)

(73) Assignee: POLLENERGIE, Saint-Hilaire-de-Lusignan (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/534,950

(22) PCT Filed: Dec. 11, 2015

(86) PCT No.: PCT/FR2015/053453
§ 371 (c)(1),
(2) Date: Jun. 9, 2017

(87) PCT Pub. No.: WO2016/092235
PCT Pub. Date: Jun. 16, 2016

(65) Prior Publication Data
US 2017/0340680 A1  Nov. 30, 2017

(30) Foreign Application Priority Data
Dec. 11, 2014  (FR) ...................... 14 62244

(51) Int. Cl.
A61K 35/644 (2015.01)
A23L 21/20 (2016.01)
A23L 33/10 (2016.01)
A61K 35/00 (2006.01)

(52) U.S. Cl.
CPC ............ *A61K 35/644* (2013.01); *A61K 35/00* (2013.01)

(58) Field of Classification Search
None
See application file for complete search history.

(56) References Cited

PUBLICATIONS

U.S. Appl. No. 14/897,978, filed Dec. 2015, Cardinault, N.*
U.S. Appl. No. 14/898,024, filed Dec. 2015, Cardinault, N.*
Kumazawa, et al., Food Chemistry, 84:329. (Year: 2004).*
Tomazevic, et al., Complement Therapies in Medicine, 21:306. (Year: 2013).*
Orsolic, et al. Med. Oncol., 27:1346. (Year: 2010).*
Castaldo, et al., Fitoterapia, 73:S1. (Year: 2002).*
Lahouel, et al., "The Flavonoids Effect Against Vinblastine, Cyclophosphamide and Paracetamol Toxicity by Inhibition of Lipid-Peroxydation and Increasing Liver Glutathione Concentration," Pathologie Biologie, vol. 52, No. 6, Jul. 2004, pp. 314-322.
Suzuki, et al., "Antitumor and Anticytopenic Effects of Aqueous Extracts of Propolis in Combination with Chemotherapeutic Agents," Cancer Biotherapy & Radiopharmaceuticals, vol. 17, No. 5, Jan. 2002, pp. 553-562.
Orsolic, et al., "Antitumor, Hematostimulative and Radioprotective Action of Water-Soluble Derivative of Propolis (WSDP)," Biomedicine and Pharmacotherapy, vol. 59, No. 10, Dec. 2005, pp. 561-570.
Marcucci, "Propolis: Chemical Composition, Biological Properties and Therapeutic Activity," Apidologie, Jan. 1995, pp. 83-99.
Ou, et al. "Development and Validation of an Improved Oxygen Radical Absorbance Capacity Assay Using Fluorescein as the Fluorescent Probe," J. Agric. Food Chem., 2001, vol. 49, pp. 4619-4626.
Popova, et al., "Validated Methods for the Quantification of Biologically Active Constituents of Poplar-Type Propolis," Phytochemical Analysis, vol. 15, 2004, pp. 235-240.
International Search Report issued in Application No. PCT/FR2015/053453, dated Mar. 16, 2016.

* cited by examiner

*Primary Examiner* — Michael Barker
(74) *Attorney, Agent, or Firm* — Young & Thompson

(57) ABSTRACT

The invention relates to the use of a composition comprising at least one extract of propolis, having at least one of the following properties: —an antioxidant value (ORAC) greater than or equal to 500 mmol TE/100 g of dry extract, —a flavones and flavonols content greater than or equal to 5.5% by weight with respect to the total weight of dry material of the extract, —a flavanones and dihydroflavanols content greater than or equal to 5% by weight with respect to the total weight of dry material of the product, in order to prevent and/or limit the side effects of chemotherapy.

8 Claims, No Drawings

USE OF A PARTICULAR EXTRACT OF PROPOLIS FOR COMBATING THE SIDE EFFECTS OF CHEMOTHERAPY

This invention relates to preventing and combating the side effects of chemotherapy.

Chemotherapy is one of the primary cancer treatments. This is an aggressive treatment that makes it possible to attack cancer cells scattered throughout the body. However, the attack on cancer cells is not sufficiently targeted and very often leads to unpleasant and negative side effects for the patient, such as a reduction in red blood cells, white blood cells, and platelets, nausea and vomiting, a significant state of fatigue, loss of hair and nails, and hepatic, renal and/or cardiac failures, etc.

It is therefore necessary to find an effective solution that can prevent and limit as much as possible the side effects that ensue from treatments by chemotherapy. Currently, there is not a satisfactory solution. In the case of too significant a reduction in red blood cells, oncologists have to slow down the chemotherapy protocol initially provided in order to allow the body time to re-synthesize its red blood cells or they have to accelerate this synthesis by injecting a growth factor, EPO, which has the drawback of promoting the growth of cancer cells as well.

A solution was recently proposed for preparing the body to be attacked by chemotherapy agents, which solution consists in administering propolis.

Propolis is a product that is produced by bees from resinous, gummy, and balsamic substances, collected on the buds of certain trees and shrubs, with which they incorporate salivary secretions therein.

Nevertheless, all of the propolis extracts are not effective, and the objective of this application is to propose an effective alternative to prevent the side effects of the chemotherapy agents by using a propolis extract that has the particular characteristics that impart this effectiveness to it and that does not interfere with the effectiveness of the chemotherapy agent.

To respond to this, the invention proposes using a composition that comprises at least one propolis extract that has at least one of the following characteristics:

A content of flavones and flavonols that is greater than or equal to 5.5% by weight in relation to the total weight of dry material of the extract, A content of flavanones and dihydroflavonols that is greater than or equal to 5% by weight in relation to the total weight of dry material of the extract, An antioxidant value (ORAC) that is greater than or equal to 500 mmol of TE/100 g of dry extract for its use as a health product for preventing and/or limiting the side effects of chemotherapy in humans or animals.

In particular, the object of the invention is a composition that comprises at least one such propolis extract for its application as a health product, in particular as a human oral nutritional supplement or as a medication for preventing and/or limiting the side effects of chemotherapy. Preferably, the composition is a (Dietary) Food (Intended) for Special Medical Purposes (FSMP).

Surprisingly enough, the particular propolis extract according to the invention has good effectiveness as regards preventing and/or limiting the side effects of chemotherapy, without limiting the action thereof on cancer cells.

The invention is now described in detail.

The object of the invention is therefore a composition that comprises at least one propolis extract, with said propolis extract having at least one of the following characteristics:

A content of flavones and flavonols that is greater than or equal to 5.5% by weight in relation to the total weight of dry material of the extract, A content of flavanones and dihydroflavonols that is greater than or equal to 5% by weight in relation to the total weight of dry material of the extract, An antioxidant value (ORAC) that is greater than or equal to 500 mmol of TE/100 g of dry extract for its use for preventing and/or limiting the side effects of chemotherapy in humans or animals.

Propolis extract is defined as any collected propolis that is transformed by an extraction method that makes it possible to remove the impurities that are present in the crude extract and/or to concentrate the propolis in one or more of its components.

The propolis extract can come in any form. Preferably, it comes in the form of a powder.

The useful propolis extract according to the invention is a propolis extract that comprises at least one of the following characteristics:

An antioxidant value (ORAC) that is greater than or equal to 500 mmol of TE/100 g of dry extract, A content of flavones and flavonols that is greater than or equal to 5.5% by weight in relation to the total weight of dry material of the extract, with the flavones able to be represented in particular by chrysin and/or apigenin, and with the flavonols able to be represented in particular by kaempferol and/or galangin, A content of flavanones and dihydroflavonols that is greater than or equal to 5% by weight in relation to the total weight of dry material of the extract, with the flavanones able to be represented in particular by pinocembrin, and with the dihydroflavonols able to be represented in particular by pinobanksin.

According to a preferred variant, the useful propolis extract according to the invention is a propolis extract that necessarily has an antioxidant value (ORAC) that is greater than or equal to 500 mmol of TE/100 g of extract. The antioxidant value of a propolis extract according to the invention is determined according to the ORAC method that is described by Ou et al. (2001), in JAFC, 49 (10), 4619-4626.

Preferably, the propolis extract also has a content of flavones and flavonols that is greater than or equal to 5.5% by weight in relation to the total weight of dry material of the extract and/or a content of flavanones and dihydroflavonols that is greater than or equal to 5% by weight in relation to the total weight of dry material of the extract.

According to a second variant, the propolis extract is an extract that necessarily has a content of flavones and flavonols that is greater than or equal to 5.5% by weight in relation to the total weight of dry material of the extract.

Preferably, the propolis extract also has a content of flavanones and dihydroflavonols that is greater than or equal to 5% by weight in relation to the total weight of dry material of the extract and/or an antioxidant value (ORAC) that is greater than or equal to 500 mmol of TE/100 g of dry extract.

According to a third variant, the propolis extract necessarily has a content of flavanones and dihydroflavonols that is greater than or equal to 5% by weight in relation to the total weight of dry material of the extract.

Preferably, the propolis extract also has a content of flavones and flavonols that is greater than or equal to 5.5% by weight in relation to the total weight of dry material of the extract and/or an antioxidant value (ORAC) that is greater than or equal to 500 mmol of TE/100 g of dry extract.

Regardless of the variant, the propolis extract preferably also has a total polyphenol content that is greater than or equal to 30% by weight of dry material of the extract.

The propolis that is used can be of any well-identified botanical origin. For example, it can be poplar propolis or Baccharis propolis (Brazilian green propolis), in particular Baccharis dracunculifolia.

Very preferably, the composition comprises a poplar propolis extract.

The extract that is present in the composition can be obtained by a method that comprises the following steps:
Extraction of propolis,
Concentration for obtaining an antioxidant value (ORAC) that is greater than or equal to 500 mmol of TE/100 g of dry extract, and/or a content of flavones and flavonols that is greater than or equal to 5.5% by weight in relation to the total weight of dry material of the extract, and/or a content of flavanones and dihydroflavonols that is greater than or equal to 5% by weight in relation to the total weight of dry material of the extract, and preferably at least 30% of polyphenols by weight of dry material of the extract.

The extract can then be reconcentrated.

The different steps of the method should be carried out without destroying the active ingredients.

According to a particularly suitable embodiment, the extract that is used according to the invention can be obtained by a method that comprises the following steps:
Maceration of crude propolis in an alcohol solution, and Concentration by evaporation,
Putting into powder form according to a method for mixing the propolis paste with the negative-cold excipients for preserving the integrity of the active ingredients during this mixing.

The preceding method makes it possible to obtain a propolis powder that is very concentrated in active ingredients and lacking in waxes and other impurities contained in the raw material. With the propolis powders on the market being produced directly starting from a mixture of the raw material with excipients [sic].

The propolis extract that is obtained has at least one of the following characteristics:
An antioxidant value (ORAC) that is greater than or equal to 500 mmol of TE/100 g of dry extract,
A content of flavones and flavonols that is greater than or equal to 5.5% by weight in relation to the total weight of dry material of the extract,
A content of flavanones and dihydroflavonols that is greater than or equal to 5% by weight in relation to the total weight of dry material of the extract.

Very preferably, it comprises at least 30% by weight of total polyphenols.

The extract can then be transformed into powder.

The propolis extract that is obtained is incorporated into a composition.

The composition that comprises the propolis extract is used as a health product in humans or animals, in particular as a human oral nutritional supplement or as a medication or as a veterinary product.

Preferably, the composition according to the invention is a nutritional supplement, in particular a (Dietary) Food (Intended) for Special Medical Purposes (FSMP).

The composition according to the invention, in addition to the propolis extract, can contain proteins, carbohydrates, lipids, vitamins, and/or minerals, added in supplements. Preferably, these molecules are added according to the regulation in force on the FSMPs.

The composition can also contain excipients that are known by one skilled in the art, such as kaolin, carob powder, silica, or Fibregum®, or other texturing, liquefying, coating and gastro-resistant agents that are known in the pharmaceutical field, such as ethyl cellulose or sodium alginate or other coating and gastro-resistant agents.

According to a suitable embodiment, the composition comes in the form of a powder.

The composition according to the invention, when it is an oral nutritional supplement, is administered in addition to and/or as a substitute for meals.

In a preferred manner, the daily dose of composition comprises between 600 and 1,200 mg of propolis powder extract by weight of dry material. Preferably, the daily dose is divided into 2 or 3 servings.

The composition according to the invention that comprises at least one propolis extract according to the invention is used for its application for preventing and/or limiting the side effects of chemotherapy. It is preferably used before the administration of chemotherapy agents to prepare the cells to be attacked by the chemotherapy agents.

In particular, the composition according to the invention can be used for protecting against and/or limiting the reduction in white blood cells, red blood cells, blood platelets, or hepatic, renal or cardiac alterations following injections of chemotherapy agents.

Actually, the injection of chemotherapy agents brings about a reduction in white blood cells, red blood cells, and blood platelets, and the use of a propolis extract according to the invention makes it possible to limit this reduction.

In addition, the composition according to the invention can be used to protect against and/or to limit the free-radical damage caused by chemotherapy agents to organs, in particular to the liver, the kidneys, and/or the heart, in particular by stimulating the Nrf2 signaling path, which is involved in the cell's endogenous antioxidant defense.

Advantageously, owing to its action in particular on the limitation of the reduction in white blood cells, red blood cells, and blood platelets, and on the limitation of free-radical damage, the composition according to the invention makes it possible to prevent and/or to combat nausea, hair loss, nail loss, states of fatigue, weight loss, hepatic, renal and/or cardiac failure, and depression in individuals undergoing chemotherapy treatment.

The invention is now illustrated by examples and test results.

EXAMPLE 1: EXAMPLE OF PROPOLIS EXTRACT

The propolis that is used, in particular poplar propolis, is obtained by implementing the technique of grids, which makes it possible to obtain propolis with particular characteristics suitable for medical use in comparison to a propolis obtained by the scraping technique. The grid method makes it possible to obtain a propolis with a higher polyphenol level and a reduced percentage of wax.

Preferably, the percentage of wax in the collected propolis is less than 21%, even more preferably less than 17%.

Once the propolis is collected, it is treated by implementing an extraction method comprising the following steps:
The propolis is mixed in an extractor with alcohol according to a ratio of 1/2.5 to 1/5 (w/v) for a given time period,
The mixture then undergoes filtration so as to keep in liquid solution only the active ingredients of propolis: the polyphenols, A final clarification by gravitational decanting can optionally be carried out if necessary.

This method makes it possible to produce a liquid extract that is loaded with active ingredients and is lacking in waxes and other impurities contained in the raw material.

This liquid extract is then concentrated in terms of active ingredients by dealcoholization, with the parameters having to be adjusted to obtain a propolis extract that has the following characteristics:

An antioxidant value (ORAC) that is greater than or equal to 500 mmol of TE/100 g of dry extract, A content of flavones and flavonols that is greater than or equal to 5.5% by weight in relation to the total weight of dry material of the extract, A content of flavanones and dihydroflavonols that is greater than or equal to 5% by weight in relation to the total weight of dry material of the extract, and Preferably a total polyphenol content that is greater than or equal to 30% by weight in relation to the total weight of dry material of the extract.

A soft extract that is very concentrated in terms of active ingredients and that can be transformed into powder is then obtained.

An example of a propolis extract that is obtained by the implementation of this method is a poplar propolis extract in powder form, having the following characteristics:

An antioxidant value (ORAC) of between 500 and 750 mmol of TE/100 g of dry extract (mean value 698)

A content of flavones and flavonols of between 5.5% and 10% by weight in relation to the total weight of dry material of the extract (mean 8.6%)

A content of flavanones and dihydroflavonols of between 5% and 10% by weight in relation to the total weight of dry material of the extract (mean 7.1%)

A total polyphenol content of between 30% and 50% (mean 38.7%).

EXAMPLE 2: COMPOSITION EXAMPLE

A useful composition example according to the invention comprises:
- 65% of the extract of Example 1, and
- 10% carob powder, and/or
- 10% silica, and/or
- 15% of at least one other excipient (magnesium stearate).

EXAMPLE 3: COMPOSITION EXAMPLE

A useful composition example according to the invention comprises:
- 75% of the extract of Example 1, and
- 5% carob powder, and/or
- 10% silica, and/or
- 10% of at least one other excipient (magnesium stearate).

EXAMPLE 4: COMPOSITION EXAMPLE

A useful composition example according to the invention comprises:
- 75% of the extract of Example 1, and
- 25% kaolin.

Evaluation of the Physico-Chemical and Biological Differences of Different Propolis Extracts The characteristics of different propolis powders have been tested:
Powder according to Example 1
Powders of the prior art (commercial-grade propolis powders): powder 1 comes from Aagaard, powder 2 from Aprolis, and powder 3 from Apimab.

The dosages of total polyphenols and 2 flavonoid subfractions have been performed by spectrophotometry according to the methods that are described and validated by Popova et al. (2004), 15: 235-240 in Phytochemical Analysis.

The antioxidant value is determined according to the ORAC method that is described by Ou et al. (2001), in JAFC, 49 (10), 4619-4626.

The results are presented in the table below:

|  | Total Polyphenols (g/100 g) | Flavones and Flavonols (g/100 g) | Flavanones and Dihydroflavonols (g/100 g) | ORAC (mmol of TE/100 g) |
| --- | --- | --- | --- | --- |
| Powder of Example 1 | 38.7 | 8.3 | 7.1 | 698 |
| Powder 1 | 14.1 | 1.5 | 4.7 | 98 |
| Powder 2 | 34.4 | 7.2 | 7.2 | 480 |
| Powder 3 | 12.3 | 1.9 | 3.5 | 177 |

In-Vitro Evaluation of the Effect of Propolis on the Side Effects of Chemotherapy Measurement of the Reversion of the Chemotherapy Agent Toxicity Primary hepatocytes of rats were sampled and inoculated into a 96-well plate. 24 hours after the inoculation, the hepatocytes were treated with different doses of propolis (Example 1) for 24 hours. At the end of the 24 hours of pretreatment, the propolis is removed and the hepatocytes are treated with cytotoxic chemotherapy compounds (tamoxifen and cisplatin).

The percentage of hepatic cells that are cytolyzed after a pretreatment with different concentrations of propolis and then subjected to a cytotoxic concentration of tamoxifen (25 µM) was evaluated and presented in the table below:

| Hours | Untreated | 1 µg/ml of Propolis | 3 µg/ml of Propolis | 10 µg/ml of Propolis |
| --- | --- | --- | --- | --- |
| 0 | 4.09 | 3.54 | 4.03 | 4.04 |
| 2 | 4.04 | 3.61 | 4.08 | 4.20 |
| 4 | 4.44 | 4.02 | 4.41 | 4.19 |
| 6 | 5.67 | 5.54 | 5.21 | 4.65 |
| 8 | 7.03 | 6.92 | 5.68 | 4.80 |
| 10 | 8.75 | 8.29 | 6.32 | 4.91 |
| 12 | 10.22 | 9.78 | 6.78 | 4.96 |
| 14 | 11.71 | 10.82 | 7.11 | 5.01 |
| 16 | 12.76 | 11.89 | 7.46 | 5.03 |
| 18 | 13.85 | 12.89 | 7.68 | 4.89 |
| 20 | 14.46 | 14.16 | 7.89 | 4.85 |
| 22 | 14.94 | 14.61 | 8.21 | 4.90 |
| 24 | 15.47 | 15.28 | 8.26 | 4.98 |
| 26 | 15.87 | 15.85 | 8.54 | 5.01 |
| 28 | 16.41 | 16.09 | 8.80 | 5.13 |
| 30 | 16.60 | 16.51 | 9.00 | 4.87 |
| 32 | 17.30 | 16.90 | 9.20 | 4.68 |
| 34 | 17.94 | 17.46 | 9.20 | 4.70 |
| 36 | 18.22 | 17.42 | 9.44 | 4.45 |
| 38 | 18.67 | 18.08 | 9.74 | 4.54 |

Likewise, the percentage of hepatic cells that are cytolyzed after a pretreatment at different propolis concentrations and then subjected to a cytotoxic concentration of cisplatin (10 µM) is presented in the table below:

| Hours | Untreated | 0.1 µg/ml of Propolis | 0.3 µg/ml of Propolis | 1 µg/ml of Propolis | 10 µg/ml of Propolis |
|---|---|---|---|---|---|
| 0 | 1.31 | 1.83 | 1.78 | 2.27 | 2.10 |
| 2 | 1.11 | 1.43 | 1.01 | 1.77 | 1.67 |
| 4 | 0.99 | 1.21 | 0.67 | 1.51 | 1.37 |
| 6 | 0.95 | 1.20 | 0.60 | 1.52 | 1.29 |
| 8 | 0.92 | 1.06 | 0.57 | 1.43 | 1.28 |
| 10 | 0.89 | 1.01 | 0.48 | 1.39 | 1.14 |
| 12 | 0.85 | 1.02 | 0.57 | 1.31 | 1.06 |
| 14 | 0.86 | 1.09 | 0.69 | 1.39 | 1.16 |
| 16 | 1.15 | 1.18 | 0.92 | 1.45 | 1.28 |
| 18 | 1.42 | 1.48 | 1.08 | 1.52 | 1.29 |
| 20 | 1.90 | 1.77 | 1.52 | 2.07 | 1.74 |
| 22 | 2.82 | 2.30 | 1.83 | 2.63 | 1.87 |
| 24 | 4.29 | 3.33 | 2.98 | 3.45 | 2.30 |
| 26 | 5.82 | 4.59 | 3.96 | 4.14 | 3.33 |
| 28 | 7.68 | 6.10 | 4.81 | 5.12 | 3.98 |
| 30 | 9.70 | 7.53 | 6.44 | 6.83 | 5.58 |
| 32 | 12.48 | 9.05 | 7.98 | 8.08 | 6.27 |
| 34 | 15.01 | 11.10 | 9.25 | 9.71 | 7.66 |
| 36 | 16.84 | 12.10 | 10.28 | 10.63 | 8.37 |
| 38 | 18.49 | 13.46 | 11.43 | 11.43 | 9.22 |
| 40 | 20.46 | 15.04 | 11.93 | 12.96 | 9.71 |
| 42 | 21.74 | 15.78 | 12.68 | 14.38 | 11.02 |
| 44 | 23.61 | 17.33 | 13.59 | 14.53 | 11.10 |
| 46 | 25.68 | 18.65 | 14.18 | 15.71 | 12.14 |
| 48 | 27.07 | 19.45 | 14.71 | 16.95 | 12.34 |
| 50 | 28.48 | 20.76 | 15.36 | 16.89 | 12.94 |
| 52 | 30.37 | 22.09 | 16.65 | 17.26 | 13.28 |

Tamoxifen and cisplatin bring about a dose-dependent cytolysis of hepatocytes, where the increase in the dose induces an increase in cells cytolyzed with a complete cytolysis of between 6 and 48 hours for the highest dose.

It is noted that a pretreatment with a propolis extract according to the invention has a hepatocytic protective action against tamoxifen. It imparts protection against chemotherapy treatment that is comparable to a protective hepato compound of known reference: oltipraz.

It is also noted that the propolis extract according to the invention is able to reduce the toxic effects of cisplatin.

In-Vivo Evaluation of the Effect of Propolis on the Side Effects of Chemotherapy Wistar rats of approximately 200 g were used during this in-vivo experiment, at a rate of 8 animals per group. The animals received orally either the vehicle (gr control) or propolis (Example 1) at 12.5 mg of powder/Kg of body weight for 5 consecutive days before the injection of a chemotherapy agent (epirubicin, cyclophosphamide, 5-FU and taxotere), or the chemotherapy agents alone. The animals are sacrificed 21 days after the injection of the chemotherapy agent. The weight and the different parameters of the blood formula will be tracked in these animals on days D+1, D+6 and D+14 and D+21 post-chemotherapy injection. The contents of endogenic antioxidants (glutathione=GSH) and the hepatocytic lipid peroxidation (MDA) levels will be evaluated on D+21.

Change in Weight of the Animals of the Different Groups.

|  | D − 5 | D + 1 | D + 6 | D + 14 | D + 21 | Variation between D + 1 and D + 21 |
|---|---|---|---|---|---|---|
| Gr Control | 151.6 | 164.5 | | | | |
| Gr Epirubicin | 150.2 | 156.1 | 156.1 | 149.5 | 155.2 | −0.9 |
| Gr Epirubicin + Propolis | 157 | 163.5 | 168.6 | 171.5 | 178.4 | +14.9 |
| Gr Cyclophosphamide | 160.4 | 167.2 | 157.7 | 164 | 152.3 | −14.9 |
| Gr Cyclophosphamide + Propolis | 155.6 | 162.6 | 165.6 | 169.2 | 181.4 | +18.8 |
| Gr 5-FU | 153.5 | 157.6 | 153.7 | 147.9 | 143.7 | −13.9 |
| Gr 5-FU + Propolis | 153.6 | 158.6 | 163.4 | 167.7 | 169 | +10.4 |
| Gr Taxotere | 151.6 | 156.9 | 164.6 | 170.7 | 175.5 | +18.6 |
| Gr Taxotere + Propolis | 151.7 | 158.7 | 165.6 | 173.5 | 180.4 | +21.7 |

It is noted that the animals that are treated with the chemotherapy agents see their weight decrease rapidly after the injection (except for the taxotere). The pretreatment with the propolis extract according to the invention (Example 1) restores the treated animals' weight gain curves.

Change in Red Blood Cells of the Animals of the Different Groups.

|  | D − 5 | D + 1 | D + 6 | D + 14 | D + 21 | Variation between D + 1 and D + 21 |
|---|---|---|---|---|---|---|
| Gr Control | 6.6 | 6.2 | | | | |
| Gr Epirubicin | 6.73 | 5.95 | 5.04 | 4.72 | 3.07 | −48% |
| Gr Epirubicin + Propolis | 6.52 | 6.03 | 5.83 | 5.33 | 4.81 | −20% |
| Gr Cyclophosphamide | 6.51 | 5.94 | 4.23 | 3.80 | 3.22 | −46% |
| Gr Cyclophosphamide + Propolis | 6.69 | 6.24 | 5.84 | 5.28 | 4.60 | −26% |
| Gr 5-FU | 6.51 | 6.56 | 4.19 | 3.05 | 2.94 | −55% |
| Gr 5-FU + Propolis | 6.67 | 6.40 | 5.99 | 5.15 | 5.31 | −17% |
| Gr Taxotere | 6.39 | 6.23 | 5.18 | 4.18 | 2.95 | −52% |
| Gr Taxotere + Propolis | 6.47 | 6.23 | 5.95 | 4.92 | 4.61 | −26% |

It is known that one of the side effects of the chemotherapy agents is their ability to destroy the blood lines often leading to aplasia in individuals. The results confirm that the injection of agents brings about a very distinct and significant reduction in red blood cells—48, 45, 55, and 52% on the $21^{st}$ day post-injection for epirubicin, cyclophosphamide, 5-FU and taxotere, respectively. Regardless of the agent, the propolis extract according to the invention brings about a significant 50% reduction in the loss of red blood cells.

Change in White Blood Cells of the Animals of the Different Groups.

|  | D − 5 | D + 1 | D + 6 | D + 14 | D + 21 | Variation between D − 5 and D + 21 |
|---|---|---|---|---|---|---|
| Gr Control | 6.83 | 8.38 | | | | |
| Gr Epirubicin | 6.79 | 3.55 | 2.32 | 12.54 | 3.63 | −46% |
| Gr Epirubicin + Propolis | 6.65 | 5.76 | 4.71 | 8.40 | 5.26 | −21% |
| Gr Cyclophosphamide | 6.30 | 3.33 | 2.96 | 10.20 | 3.19 | −49% |
| Gr Cyclophosphamide + Propolis | 6.41 | 6.01 | 5.18 | 9.36 | 4.63 | −28% |
| Gr 5-FU | 6.49 | 3.91 | 2.74 | 10.82 | 3.86 | −40% |
| Gr 5-FU + Propolis | 6.65 | 5.77 | 5.18 | 9.53 | 5.67 | −15% |
| Gr Taxotere | 6.44 | 4.41 | 4.29 | 10.18 | 3.13 | −51% |
| Gr Taxotere + Propolis | 6.50 | 6 | 5.34 | 9.28 | 4.26 | −33% |

Regarding the white blood cells, the chemotherapy agents bring about a drop on the $6^{th}$ day, followed by a very distinct rise on the $14^{th}$ day, which in turn is followed by a new drop on the $21^{st}$ day. Overall, the pretreatment with the propolis extract according to the invention limits the drop in white blood cells on the $6^{th}$ day and on the $21^{st}$ day.

Variation of the Contents of Plasmatic Creatinine in the Animals of the Different Groups.

|  | D − 5 | D + 1 | D + 21 | Variation between D − 5 and D + 21 |
|---|---|---|---|---|
| Gr Control | 6.17 | 6.33 | | |
| Gr Epirubicin | 7.13 | 10.89 | 11.39 | +60% |
| Gr Epirubicin + Propolis | 7 | 9.3 | 9.4 | +34% |
| Gr Cyclophosphamide | 6.38 | 7.25 | 10.14 | +59% |
| Gr Cyclophosphamide + Propolis | 6.38 | 6 | 6.13 | −4% |
| Gr 5-FU | 7.25 | 9 | 10.19 | +41% |
| Gr 5-FU + Propolis | 8.25 | 7.29 | 8.81 | +7% |
| Gr Taxotere | 7.60 | 8.91 | 11.53 | +52% |
| Gr Taxotere + Propolis | 7.81 | 7.80 | 8.90 | +14% |

The dosage of the plasmatic creatinine, a reflection of the functionality of the kidneys, shows that the injection of different chemotherapy agents brings about a more or less marked elevation of this parameter at D+1 and D+21, reflecting a renal attack. The pretreatment with the propolis extract according to the invention reduces plasmatic creatinine and even restores it to its base level.

Variation of the Contents of Plasmatic Glutathione in the Animals of the Different Groups.

|  | D − 5 | D + 21 | Variation between D − 5 and D + 21 |
|---|---|---|---|
| Gr Control | 20.92 | | |
| Gr Epirubicin | 23.86 | 12.83 | −46% |
| Gr Epirubicin + Propolis | 22.80 | 20.35 | −11% |
| Gr Cyclophosphamide | 26.39 | 23.81 | −10% |
| Gr Cyclophosphamide + Propolis | 22.79 | 23.20 | +2% |
| Gr 5-FU | 22.14 | 17.65 | −20% |
| Gr 5-FU + Propolis | 22.71 | 24.67 | +8% |
| Gr Taxotere | 22.88 | 16.83 | −26% |
| Gr Taxotere + Propolis | 23.61 | 23.61 | 0 |

Variation of the Contents of Plasma MDA in the Animals of the Different Groups.

|  | D − 5 | D + 21 | Variation between D − 5 and D + 21 |
|---|---|---|---|
| Gr Control | 46.08 | | |
| Gr Epirubicin | 46.61 | 85.45 | +83% |
| Gr Epirubicin + Propolis | 45.91 | 58.62 | +28% |
| Gr Cyclophosphamide | 43.78 | 79.10 | +48% |
| Gr Cyclophosphamide + Propolis | 44.49 | 52.26 | +17% |
| Gr 5-FU | 44.49 | 62.85 | +41% |
| Gr 5-FU + Propolis | 41.66 | 47.31 | +13% |
| Gr Taxotere | 45.90 | 86.16 | +88% |
| Gr Taxotere + Propolis | 43.07 | 63.56 | +47% |

The chemotherapy agents also have an impact on the primary intracellular antioxidant: glutathione (GSH) and on oxidative damage through the formation of diene conjugates, which is a reflection of the lipid peroxidation of the cellular membranes (the MDA) on the plasmatic level. These two measurements are complementary since normally a correct level of GSH makes it possible to maintain a relatively low level of MDA.

It is noted that the injection of epirubicin, 5-FU, and taxotere brings about a very distinct significant decrease in the level of plasma GSH on the $21^{st}$ day (and a little less distinct for the cyclophosphamide). In parallel, the MDA levels are multiplied by 2 for all of the chemotherapy agents on the $21^{st}$ day. The pretreatment with the propolis extract according to the invention (Example 1) makes it possible to keep the GSH level at its base level regardless of the chemotherapy agent that is used. At the same time, the MDA levels of the animals pretreated with the propolis extract according to the invention (Example 1) are significantly reduced compared to the groups that are treated with the chemotherapy agents alone.

The invention claimed is:

1. A nutritional supplement or pharmaceutical composition comprising:
   a core comprising:
      at least one concentrated propolis extract powder, with said propolis extract powder having a total polyphenol content between 38.7% and 50% by weight in relation to the total weight of dry material of the extract powder and having each of the following characteristics:
      An antioxidant value (ORAC) that is between 698 and 750 mmol of TE/100 g of dry material of the extract powder,
      A content of flavones and flavonols that is between 5.5% and 10% by weight in relation to the total weight of dry material of the extract powder,
      A content of flavanones and dihydroflavonols that is between 5% and 10% by weight in relation to the total weight of the dry material of the extract powder product;
      wherein the propolis extract powder derives from a propolis collected by a grid method, and the propolis collected by the grid method has a wax content of less than 17%; and
   a gastro-resistant coating enveloping the core;
      wherein the composition is capable of preventing and/or limiting the side effects of chemotherapy in humans or animals.

2. The composition according to claim 1, wherein the propolis extract powder is a poplar propolis extract powder.

3. The composition according to claim 1, capable of limiting and/or protecting against the reduction in white blood cells, red blood cells, and blood platelets consecutive to injections of chemotherapy agents.

4. The composition according to claim 1, capable of protecting against and/or limiting the free-radical damage caused by the chemotherapy agents to organs.

5. The composition according to claim 1, capable of protecting against and/or limiting the free-radical damage caused by chemotherapy agents to the liver, the kidneys, and/or the heart.

6. The composition according to claim 1, capable of preventing and/or combating nausea, hair loss, nail loss, states of fatigue, weight loss, and depression in individuals undergoing chemotherapy treatment.

7. The composition according to claim 1, further comprising proteins, carbohydrates, lipids, vitamins, and/or minerals.

8. A method for substituting or adding to a meal, comprising administering the composition according to claim 1.

* * * * *